United States Patent
Varley

(10) Patent No.: US 9,592,134 B2
(45) Date of Patent: Mar. 14, 2017

(54) PROSTHETIC OR ROBOT PART

(71) Applicant: RSL Steeper Group Limited, Rochester, Kent (GB)

(72) Inventor: Edward William Varley, Marsden (GB)

(*) Notice: Subject to any disclaimer, the term of this patent is extended or adjusted under 35 U.S.C. 154(b) by 0 days.

(21) Appl. No.: 14/050,489

(22) Filed: Oct. 10, 2013

(65) Prior Publication Data

US 2014/0107805 A1   Apr. 17, 2014

(30) Foreign Application Priority Data

Oct. 11, 2012   (GB) .................................. 1218291.1

(51) Int. Cl.
*A61F 2/58* (2006.01)
B25J 15/00 (2006.01)
*A61F 2/68* (2006.01)
*A61F 2/70* (2006.01)

(52) U.S. Cl.
CPC ........... *A61F 2/586* (2013.01); *B25J 15/0009* (2013.01); *A61F 2002/6836* (2013.01); *A61F 2002/701* (2013.01)

(58) Field of Classification Search
CPC .. A61F 2/54; A61F 2/586; A61F 2/588; A61F 2/58; B25J 15/0009
See application file for complete search history.

(56) References Cited

U.S. PATENT DOCUMENTS

2003/0195637 A1* 10/2003 Shen .................... A61F 2/60
   623/44
2012/0185061 A1* 7/2012 Caron L'Ecuyer ..... A61F 2/586
   623/64
2013/0030550 A1* 1/2013 Jopek et al. .................... 623/64

FOREIGN PATENT DOCUMENTS

WO   2010018358 A2   2/2010
WO   2012039479 A1   3/2012

* cited by examiner

*Primary Examiner* — Bruce E Snow
(74) *Attorney, Agent, or Firm* — Daniel A. Tallitsch; Baker & McKenzie LLP

(57) ABSTRACT

A prosthetic or robot part, comprising a base, a proximal and a distal. The proximal is mounted on the base so as to be rotatable thereabout in a given sense. The distal is mounted on the proximal so as to be rotatable thereabout in the same sense to effect a gripping action of the prosthetic or robot part. The proximal and the distal are rotatable in the opposite sense to release the grip. One part of a drive of the part is pivoted to the base about a base pivot axis. Another part of the drive is pivoted to the distal about a distal pivot axis. The distal is also pivoted to the proximal about the said distal pivot axis. Thus the proximal, the distal and the said another part of the drive are all pivotable relative to one another about the said distal pivot axis.

12 Claims, 3 Drawing Sheets

PROSTHETIC OR ROBOT PART

CROSS-REFERENCE TO RELATED APPLICATION

This application claims priority to United Kingdom Patent Application No. 1218291.1 filed on Oct. 11, 2013, which is incorporated herein by reference.

The present invention relates to a prosthetic or robot part, comprising a base, a proximal and a distal, in which the proximal is mounted on the base so as to be rotatable thereabout in a given sense, and the distal is mounted on the proximal so as to be rotatable thereabout in the same sense to effect a gripping action of the prosthetic or robot part, the proximal and the distal being rotatable in the opposite sense to release the grip.

US-A-2011160873 discloses a prosthetic finger in which a rod connected to an actuator is coupled to operate tendons which extend along a proximal and a middle phalanx. Operation of the actuator in one sense causes a gripping action of the finger prosthesis, and in the opposite sense releases the grip. The proximal and the middle phalanx may be sprung-loaded towards an open position. Such a construction is heavy, complex and cumbersome, and incurs a limitation on the control of grip that is obtainable.

The present invention seeks to provide a remedy to one or more of these disadvantages.

Accordingly the present invention is directed to a prosthetic or robot part having the construction set out in the opening paragraph of the present specification, characterised in that one part of a drive of the part is pivoted to the base about a base pivot axis and another part of the drive is pivoted to the distal about a distal pivot axis, the distal also being pivoted to the proximal about the said distal pivot axis, so that the proximal, the distal and the said another part of the drive are all pivotable relative to one another about the said distal pivot axis.

Preferably the said drive is a helical drive, and may comprise a motor, from which extends a screw shaft which is rotatable about its elongate axis by the motor, the motor and a screw shaft together constituting one or other of the said parts of the drive. The other of the said parts of the drive may be constituted by a nut through which is threaded the screw shaft. Preferably, the said nut constitutes the said another part of the drive.

The prosthetic or robot part may further comprise an upper bar extending alongside the proximal and pivoted at one end to the distal about a second distal pivot axis spaced apart from the first-mentioned distal pivot axis and pivoted at its other end to a portion adjacent to the base about an axis which is spaced from and is movable relative to the said base pivot axis.

The said portion may be constituted by a base link which is also pivoted about the said base pivot axis.

The proximal may also be pivoted to the base about a second base pivot axis spaced apart from the first-mentioned base pivot axis.

The prosthetic or robot part may comprise a prosthetic finger.

The present invention extends to a partial hand which includes such a prosthetic finger. It also extends to a prosthetic hand which includes such a prosthetic finger.

An example of a prosthetic or robot part made in accordance with the present invention will now be described in greater detail with reference to the accompanying drawings, in which.

Figure 1:
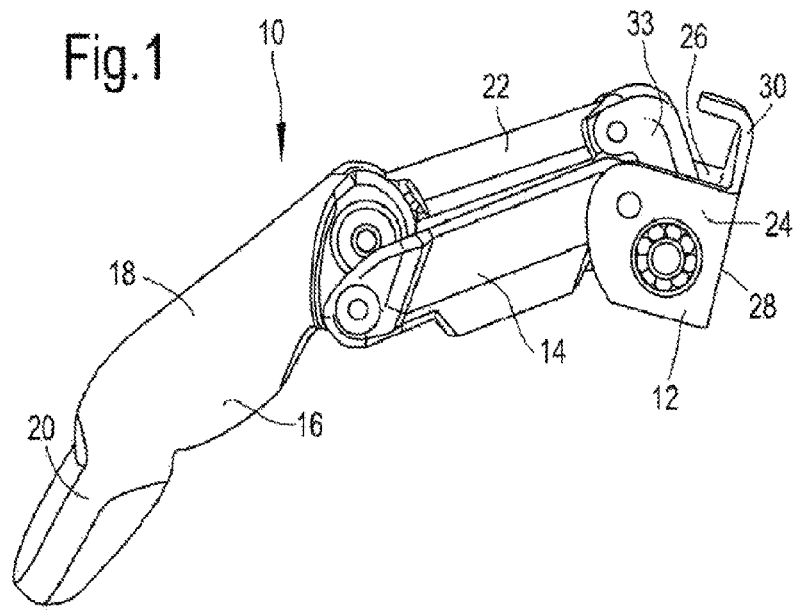
FIG. 1 shows a side perspective view of a prosthetic finger which embodies the present invention.

The prosthetic finger 10 shown in FIG. 1 has a base or knuckle 12, a proximal constituted by a proximal link 14, and a distal 16. The proximal link 14 corresponds to a proximal phalanx of an actual finger, and the distal 16 corresponds to the middle phalanx and the distal phalanx combined of an actual human finger. Thus the distal 16 comprises a middle phalanx portion 18 and a distal phalanx portion 20, further from the knuckle than the middle phalanx portion 18, there being a slight bend between the portions 18 and 20, whilst the portions 18 and 20 are constituted by a single rigid part made of a synthetic plastics material, being the distal 16.

The prosthetic finger 10 is also provided with an upper bar 22 which is movable relative to the proximal link 14 in a generally longitudinal direction, as described in greater detail hereinafter.

The knuckle 12 has a generally U-shaped section comprising two generally parallel side plates 24 and 26 interconnected by means of a connecting part 28. An angled portion 30 of the knuckle 12 extends from the connecting portion 28 from that end thereof closer to the bar 22, and provides a guide for a cover or skin (not shown) for the finger prosthesis 10.

Figure 2:
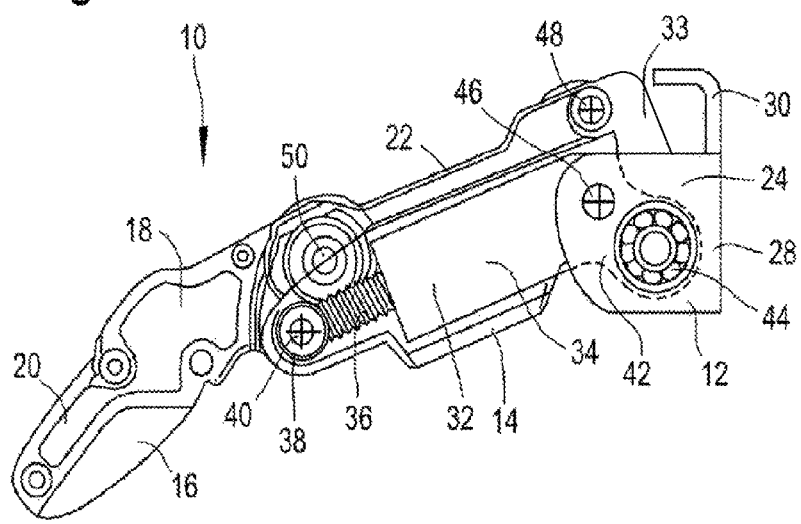
FIG. 2 shows a side, axial sectional, see-through view of the prosthetic finger shown in FIG. 1.

The proximal link 14 comprises a shell-like cover which encloses a drive 32 which is not visible in FIG. 1 but which can be seen clearly in the sea-through view of FIG. 2.

A knuckle link 33 connects a knuckle end of the upper bar 22 to the knuckle 12, the other end of the bar 22 being connected to one end of the distal 16.

The manner in which the various parts of the finger prosthesis 10 are connected is by way of a number of pivots, as now described in greater detail.

Thus the drive 32, which comprises a generally cylindrical motor 34 extending longitudinally within the proximal link 14, and an externally threaded leadscrew or screw shaft 36 extending longitudinally along the drive axis of the motor 34 in a direction therefrom towards the distal 16. The screw shaft 36 engages an internally screw threaded nut 38 connected to the distal 16 by way of a lower pivot 40 at an end of the distal 16 closer to the proximal link 14. The proximal link 14 and the distal 16 are also pivotally connected to one another at their respective adjacent ends to pivot about the axis of the pivot 40, so that the nut 38, the proximal link 14 and the distal 16 are all pivotable relative to one another about the axis of the pivot 40.

A lug 42 of the drive 32, at a knuckle end thereof, is pivotally connected to the knuckle 12, the lug 42 being rigidly connected to the knuckle end of the motor 34. The pivotal connection between the lug 42 and the knuckle 12 is by way of a ball bearing pivot 44 in the knuckle 12 so that the knuckle 12 and the drive 32 are pivotable relative to one another about the pivotal 44.

The knuckle end of the proximal link 14 is connected to the knuckle 12 at a pivot 46 which is spaced from the pivot 44 in a direction towards the upper bar 22.

The knuckle link 33 is connected at its lower end to the knuckle 12 so as to be pivotable relative thereto about the pivot axis of the pivot 44. The upper end of the knuckle link 33 is connected to a knuckle end of the upper bar 22 at a further pivot 48 so that the knuckle link 33 and the upper bar 22 are pivotable relative to one another about the pivot 48.

The distal end of the upper bar 22 is connected to the distal 16 at a pivot 50 which is spaced from the pivot 40 in an upward direction viewing the finger prosthesis 10 as in the Figures, and in a direction towards the knuckle 12.

When the finger prosthesis 10 shown in the Figures is ready for use, the motor 34 is connected to the circuit (not shown) comprising a battery by means via a switch operable by a myoelectric electrode.

Figure 3:
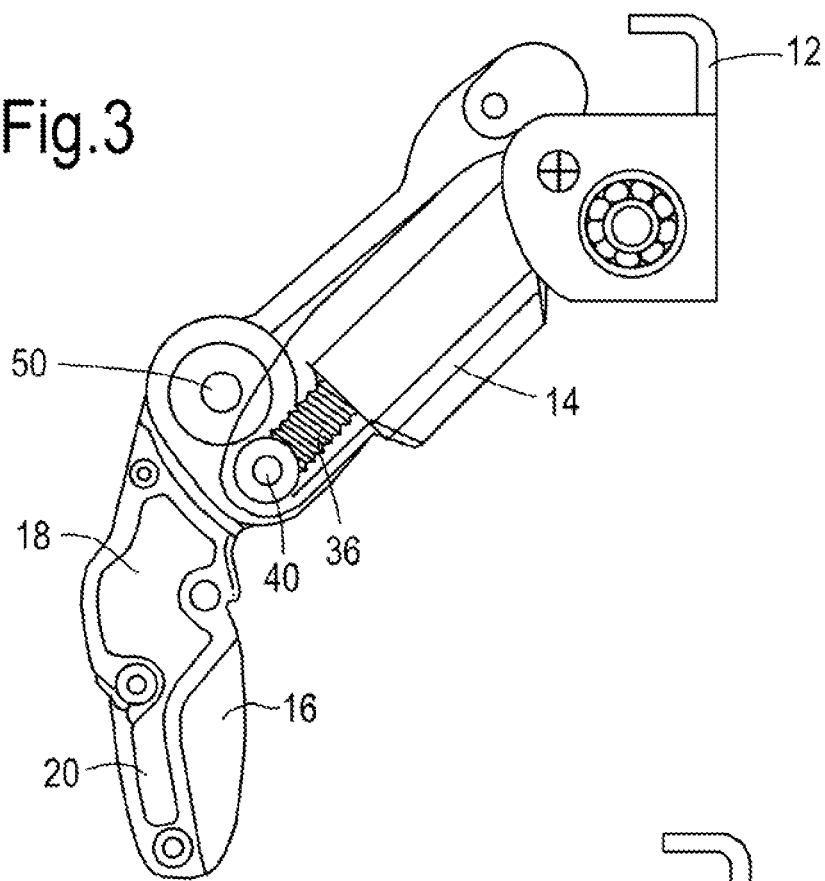
FIG. 3 shows on a smaller scale a view of the prosthetic finger shown in FIG. 1 corresponding to FIG. 2 but with the prosthetic finger in a partially gripping position.
Figure 4:
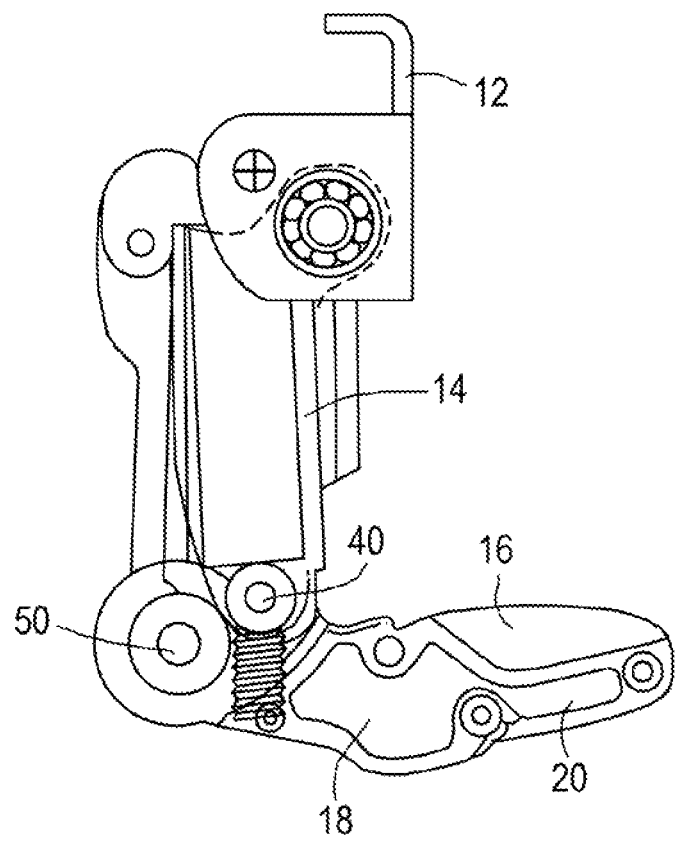
FIG. 4 shows a view corresponding to FIG. 3 but with the prosthetic finger in a fully gripping position.
Figure 5:
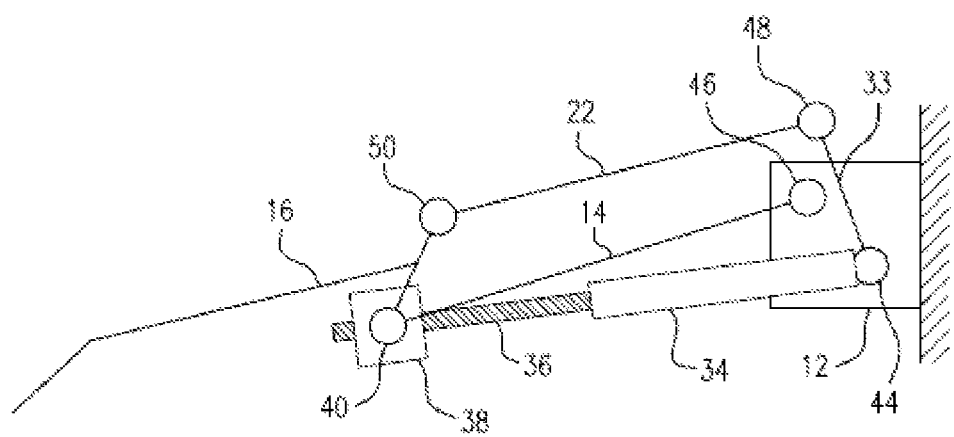
FIG. 5 shows a simplified representation of the kinematic connection of the various elements of the prosthetic finger.

Operation of the motor 34 to drive the screw shaft 36 in a sense which draws the nut 38 towards the knuckle 12 causes the drive 32 and the proximal link 14 to rotate in a downward direction viewing the finger prosthesis 10 as in the Figures, the proximal link 14 and the drive 32 rotating by slightly different respective amounts by virtue of the different pivot axes they rotate about relative to the knuckle 12. Furthermore, by virtue of the linkage of the upper part of the proximal end of the distal 16 to the knuckle 12 via the upper bar 22 and the knuckle link 33, the distal 16 is rotated about the pivot 40 faster than the rate at which the proximal link 14 rotates about the knuckle 12, so that the distal 16 rotates inwardly relative to the proximal link 14, and the finger prosthesis 10 as a whole performs a gripping action, the relative positions of its various components changing from what is shown in FIG. 2 to what is shown in FIG. 3, and from there to what is shown in FIG. 4. In this way the screw shaft 36 acts on both the proximal link 14 and the distal 16.

Drive of the motor 34 in the opposite sense causes release of the grip.

The natural friction between the nut 38 and the screw shaft 36 is sufficient to enable the finger prosthesis 10 to maintain a grip even against a force which urges the finger prosthesis towards its open position, without any force being exerted by the motor 34. This provides a considerable saving in energy consumption.

Numerous variations and modifications to the illustrated prosthesis 10 may occur to the reader without taking the result construction outside the scope of the present invention. For example, the drive 32 may comprise a different kind of helical drive, for example it might comprise a ball screw arrangement. An advantage of such a construction would be the reduced friction during operation of the drive 32. A disadvantage would be that there would be inadequate friction to inhibit a force acting on the prosthesis to release a grip, so that the motor 32 would need to maintain a force on the distal 16 to hold the grip.

The portions 18 and 20 could be made so that they are pivotable relative to one another, with further connections to the drive or a further drive to enable a full gripping action of the finger prosthesis 10.

The invention claimed is:

1. A prosthetic or robot part, comprising a base, a proximal segment and a distal segment, in which the proximal segment is mounted on the base so as to be rotatable thereabout in a first direction, and the distal segment is mounted on the proximal segment so as to be rotatable thereabout in the first direction to effect a gripping action of the prosthetic or robot part, the proximal segment and the distal segment being rotatable in a second direction which is opposite to the first direction to release the grip, wherein a first part of a drive of the prosthetic or robotic part is pivoted to the base about a base pivot axis and a second part of the drive is pivoted to the distal segment about a distal pivot axis, the distal segment also being pivoted to the proximal segment about the said distal pivot axis, so that the proximal segment, the distal segment and the said second part of the drive are all pivotable relative to one another about the said distal pivot axis, and wherein said drive is a helical drive.

2. A prosthetic or robot part according to claim 1, wherein the said drive comprises a motor, from which extends a screw shaft which is rotatable about its elongate axis by the motor, the motor and a screw shaft together constituting the first part of the drive.

3. A prosthetic or robot part according to claim 2, wherein the second part is constituted by a nut through which is threaded the screw shaft.

4. A prosthetic or robot part according to claim 3, wherein the said nut constitutes the said another part of the drive.

5. A prosthetic or robot part according to claim 2, wherein the first part is constituted by a nut through which is threaded the screw shaft.

6. A prosthetic or robot part according to claim 1, wherein it further comprises an upper bar extending alongside the proximal segment and pivoted at one end of the distal segment about a second distal pivot axis spaced apart from the first-mentioned distal pivot axis and pivoted at its other end to a segment adjacent to the base about an axis which is spaced from and is movable relative to the said base pivot axis.

7. A prosthetic or robot part according to claim 6, wherein the said segment is constituted by a base link which is also pivoted about the said base pivot axis.

8. A prosthetic or robot part according to claim 1, wherein the proximal segment is pivoted to the base about a second base pivot axis spaced apart from the base pivot axis.

9. A prosthetic or robot part according to claim 1, wherein it comprises a prosthetic finger.

10. A partial artificial hand which includes a prosthetic finger as claimed in claim 9.

11. An artificial hand which includes a prosthetic finger as claimed in claim 9.

12. A prosthetic or robot part according to claim 1, wherein the said drive comprises a motor, from which extends a screw shaft which is rotatable about its elongate axis by the motor, the motor and a screw shaft together constituting the second part of the drive.

* * * * *